United States Patent
Masuda et al.

(10) Patent No.: US 7,495,094 B2
(45) Date of Patent: Feb. 24, 2009

(54) **DETECTION REAGENT FOR THERMOSTABLE DIRECT HEMOLYSIN-RELATED HEMOLYSIN GENE OF *VIBRIO PARAHAEMOLYTICUS***

(75) Inventors: Noriyoshi Masuda, Meguro-ku (JP); Ryuichi Horie, Zama (JP); Kiyoshi Yasukawa, Kawasaki (JP)

(73) Assignee: Tosoh Corporation, Shunan-shi (JP)

( * ) Notice: Subject to any disclaimer, the term of this patent is extended or adjusted under 35 U.S.C. 154(b) by 0 days.

(21) Appl. No.: 10/928,159

(22) Filed: Aug. 30, 2004

(65) Prior Publication Data

US 2005/0112628 A1 May 26, 2005

(30) Foreign Application Priority Data

Sep. 5, 2003 (JP) ............................ 2003-314142

(51) Int. Cl.
*C07H 21/04* (2006.01)
*C12Q 1/68* (2006.01)
*C12P 19/34* (2006.01)

(52) U.S. Cl. ....................... 536/24.33; 435/6; 435/91.2; 536/23.1; 536/24.3; 536/24.32

(58) Field of Classification Search ........................ None
See application file for complete search history.

(56) References Cited

U.S. PATENT DOCUMENTS

| | | | |
|---|---|---|---|
| 5,814,447 | A | 9/1998 | Ishiguro et al. |
| 6,036,572 | A | 3/2000 | Sze |
| 6,541,205 | B1 | 4/2003 | Yokoyama et al. |
| 6,562,955 | B2 | 5/2003 | Ishizuka et al. |
| 2001/0053519 | A1 * | 12/2001 | Fodor et al. .................... 435/6 |
| 2003/0176687 | A1 | 9/2003 | Ishizuka et al. |
| 2004/0115718 | A1 | 6/2004 | Ishiguro et al. |

FOREIGN PATENT DOCUMENTS

| | | |
|---|---|---|
| EP | 1 134 292 A2 | 9/2001 |
| EP | 1134292 A2 * | 9/2001 |
| WO | WO 9741260 A2 * | 11/1997 |
| WO | WO 03/033702 | 4/2003 |

OTHER PUBLICATIONS

Buck, et al. Design strategies and performance of custom DNA sequencing primers. Sep. 1999. Biotechniques, vol. 27, pp. 528-536.*
CD-ROM containing an unbridged electronic version of the article on the "Preparaion and Utilization of Isolated and Purified Oligonucleotides" by Dr. Andrew Chin.
Masamichi Kishishita, et al., "Sequence Variation in the Thermostable Direct Hemolysin-Related Hemolysin (trh) Gene of Vibrio parahaemolyticus", Applied and Environmental Microbiology, vol. 58, No. 8, XP-009012050, Aug. 1992, pp. 2449-2457.
Jun Tada, et al., "Detection of the Thermostable Direct Hemolysin Gene (tdh) and the Themostable Direct Hemolysin-related Hemolysin Gene (trh) of Vibrio Parahaemolyticus by Polymerase Chain Reaction", Molecular and Cellular Probes, vol. 6, Dec. 1992, pp. 477-487.

* cited by examiner

*Primary Examiner*—Young J Kim
*Assistant Examiner*—Samuel Woolwine
(74) *Attorney, Agent, or Firm*—Oblon, Spivak, McClelland, Maier & Neustadt, P.C.

(57) ABSTRACT

A detection reagent for detecting thermostable direct hemolysin-related hemolysin (TRH) gene in an amplification process which specifically amplifies TRH1 and TRH2 RNA, which reagent comprises a first primer having a sequence complementary to a specific sequence of an RNA derived from the TRH gene, and a second primer having a sequence homologous to said specific sequence.

8 Claims, 3 Drawing Sheets

(A)

(B)

DETECTION REAGENT FOR THERMOSTABLE DIRECT HEMOLYSIN-RELATED HEMOLYSIN GENE OF *VIBRIO PARAHAEMOLYTICUS*

FIELD OF THE INVENTION

The present invention relates to a detection reagent for detecting *Vibrio parahaemolyticus* in clinical examinations, public health examinations, food evaluations and food poisoning examinations.

PRIOR ART

*Vibrio parahaemolyticus* is commonly known as a causative organism of infectious food poisoning. In contrast to 95% or more of *Vibrio parahaemolyticus* isolated from gastroenteritis patients being Kanagawa phenomenon-positive bacteria demonstrating hemolytic activity in Wagatsuma medium, 99% of the bacteria isolated from fish and water are Kanagawa phenomenon-negative. Thus, there is considered to be a close relationship between pathogenic *Vibrio parahaemolyticus* and the Kanagawa phenomenon.

Subsequently, the Kanagawa phenomenon was determined to occur due to the release of the thermostable direct hemolysin (TDH) of *Vibrio parahaemolyticus* outside the bacterial cells, which led to increasing attention being focused on *Vibrio parahaemolyticus* as a pathogenic factor. The TDH gene is currently known to exist as five types of gene consisting of TDH1 to TDH5.

More recently, from a microbial strain that demonstrates pathogenicity despite being negative for the Kanagawa phenomenon, a hemolysin having a base sequence similar to TDH as well as having partial common antigenicity had been identified (TDH-related hemolysin [TRH]). The TRH gene is currently known to exist as two types consisting of TRH1 and TRH2.

Although methods for detecting and identifying *Vibrio parahaemolyticus* comprising evaluation for Kanagawa phenomenon following enrichment culturing or isolation culturing are known, methods which detect a specific sequence present in the *Vibrio parahaemolyticus* gene or an RNA derived from said gene following the amplification of such a sequence are preferable in terms of sensitivity, speed and ease of procedure. A method that amplifies a target nucleic acid at a constant temperature is particularly preferable in terms of automation of a testing system.

A method for detecting and identifying *Vibrio parahaemolyticus* has been reported in which an RNA derived from TRH1 or TRH2 gene is specifically amplified at a comparative low temperature (41° C.) (Japanese Unexamined Patent Publication Nos. 2001-258569, 2001-340087 and 2001-340088). In this method, an RNA amplification process is used in which a double-strand RNA-DNA is formed by producing a cDNA with an RNA-dependent DNA polymerase using a specific sequence of an RNA derived from said TRH1 or TRH2 gene as a template, as well as a first primer having a sequence complementary to said specific sequence, and a second primer having a sequence homologous to said specific sequence, wherein the first primer or second primer has a sequence in which a promoter sequence of an RNA polymerase is added to the 5' end of one of the primers, degrading the RNA of the double-strand RNA-DNA by ribonuclease H, thereby producing a single-strand DNA, and producing a double-strand DNA having the promoter sequence capable of transcribing the RNA composed of the RNA sequence or the sequence complementary to the RNA sequence with a DNA-dependent DNA polymerase using said single-strand DNA as a template, wherein said double-strand DNA produces an RNA transcription product in the presence of the RNA polymerase, and said RNA transcription product serves as a template for the subsequent cDNA synthesis with the RNA-dependent DNA polymerase.

However, the aforementioned method has the following problems. First, it has low sensitivity. According to Japanese Unexamined Patent Publication No. 2001-340087, data is only indicated for the detection of TRH1 RNA for which the initial RNA amount is at least $10^3$ copies, and it is unclear as to whether TRH1 RNA can be detected if the initial RNA amount is less than $10^3$ copies (e.g., $10^2$ copies). According to Japanese Unexamined Patent Publication No. 2001-340088, data is only indicated for the detection or TRH2 RNA for which the initial RNA amount is at least $10^3$ copies, and it is unclear as to whether TRH2 RNA can be detected if the initial RNA amount is less than $10^3$ copies (e.g., $10^2$ copies).

The second problem is that any reagent capable of detecting both TRH1 and TRH2, which is required for practical use, was not reported. For example, according to Japanese Unexamined Patent Publication No. 2001-340087, the reagent capable of detecting TRH1 RNA at an initial RNA amount of at least $10^3$ copies does not detect TRH2. In addition according to Japanese Unexamined Patent Publication No. 2001-340088, the reagent capable of detecting TRH2 RNA at an initial RNA amount of at least $10^3$ copies does not detect TRH1.

Thirdly, there is no data relating to the speed of the detection. On the basis of Japanese Unexamined Patent Publication Nos. 2001-340087 and 2001-340088, only the electrophoresis patterns that were obtained after 30 minutes from the start of the reaction are disclosed, while their reaction speed is unclear.

Therefore, the object of the present invention is to provide a detection reagent for TRH RNA that has superior sensitivity and speed, and detects both TRH1 and TRH2 of *Vibrio parahaemolyticus*.

DISCLOSURE OF THE INVENTION

As a result of extensive studies to develop a detection reagent for the thermostable direct hemolysin-related hemolysin (TRH)RNA of *Vibrio parahaemolyticus* having a superior sensitivity and a higher speed, the inventors of the present invention developed a reagent capable of detecting either TRH1 or TRH2, at an initial RNA amount of $10^3$ copies, within a period of 20 minutes.

The present invention relates to a detection reagent for use in detecting the TRH gene of *Vibrio parahaemolyticus* present in a sample that is used in a detection method using an RNA amplification process comprising the steps of:

producing a cDNA with an RNA-dependent DNA polymerase using a specific sequence of an RNA derived from said TRH gene, that is, at least a partial sequence of said RNA, as a template, as well as a first primer having a sequence complementary to said specific sequence, and a second primer having a sequence homologous to said specific sequence, thereby forming a double-strand RNA-DNA, wherein either the first primer or the second primer has a sequence in which a promoter sequence of an RNA polymerase has been added to its 5' end;

degrading the RNA portion of said double-strand RNA-DNA by ribonuclease H, thereby producing a single-strand DNA; and producing a double-strand DNA having said promoter sequence capable of transcribing the RNA composed of the specific sequence of the RNA or the sequence complementary to said specific sequence of the RNA with a DNA-dependent DNA polymerase using said single-strand DNA as a template; wherein, the double-strand DNA produces an RNA transcription product in the presence of the RNA polymerase, and said RNA transcription product serves as a template for the subsequent cDNA synthesis with the RNA-dependent DNA polymerase;

which reagent comprises, as the first primer, an oligonucleotide consisting of at least 10 contiguous bases of the sequence listed as SEQ. ID No. 2, or an oligonucleotide in which one or more of the nucleotides in the oligonucleotide consisting of at least 10 contiguous bases listed as SEQ. ID No. 2 are deleted, substituted or added and is capable of specifically binding to the specific sequence, or an oligonucleotide that hybridizes under a highly stringent condition with the oligonucleotide consisting of at least 10 contiguous bases of the sequence listed as SEQ. ID No. 2 and is capable of specifically binding to the specific sequence; and as the second primer, an oligonucleotide consisting of at least 10 contiguous bases of the sequence listed as SEQ. ID No. 1, or an oligonucleotide in which one or more of the nucleotides in the oligonucleotide consisting of at least 10 contiguous bases listed as SEQ. ID No. 1 are deleted, substituted or added and is capable of specifically binding to the sequence complementary to said specific sequence, or an oligonucleotide that hybridizes under a highly stringent condition with the oligonucleotide consisting of at least 10 contiguous bases of the sequence listed as SEQ. ID No. 1 and is capable of specifically binding to the sequence complementary to said specific sequence.

The highly stringent condition refers to hybridization conditions and, for example, those indicated in the following examples consisting of carrying out a hybridization at a temperature of 44° C. in the presence of 60 mM Tris, 17 mM magnesium chloride, 100 to 130 mM potassium chloride and 1 mM DTT.

Preferably, the aforementioned first primer may be an oligonucleotide consisting of the sequence listed as SEQ. ID No. 2, and the aforementioned second primer may be an oligonucleotide consisting of the sequence listed as SEQ. ID No. 1.

Furthermore, in the case of detecting an RNA complementary to the RNA derived from the TRH gene, an oligonucleotide having a sequence complementary to the aforementioned first primer with its sequence from the 5' end to the 3' end being reversed should be used as the first primer and an oligonucleotide having a sequence complementary to the aforementioned second primer with its sequence from the 5' end to the 3' end being reversed should be used as the second primer.

Preferably, the aforementioned RNA amplification process is carried out in the presence of a cleaving oligonucleotide that cleaves the aforementioned target RNA at the 5' end of the aforementioned specific sequence and has a sequence complementary to the region adjacent to and overlapping with the 5' end of said specific sequence. Said oligonucleotide is preferably an oligonucleotide consisting of the sequence listed as SEQ. ID No. 4, 5 or 6.

More preferably, the aforementioned RNA amplification process is carried out in the presence of an oligonucleotide labeled with an intercalator fluorescent pigment, and the detection of the thermostable direct hemolysin-related hemolysin of *Vibrio parahaemolyticus* is carried out by measuring the fluorescent intensity of the reaction solution. Here, the sequence of said oligonucleotide is complementary to at least a portion of the sequence of the mRNA transcription product, and in the situation where complementary binding of said oligonucleotide to said RNA transcription product occurs, the fluorescent properties of the reaction solution change in comparison with the situation where no complex is formed.

Preferably, the aforementioned oligonucleotide consists of at least 10 contiguous bases in any of the sequences listed as SEQ. ID No. 3.

The following provides a detailed explanation of the present invention.

BEST MODE FOR CARRYING OUT THE INVENTION

Figure 1:
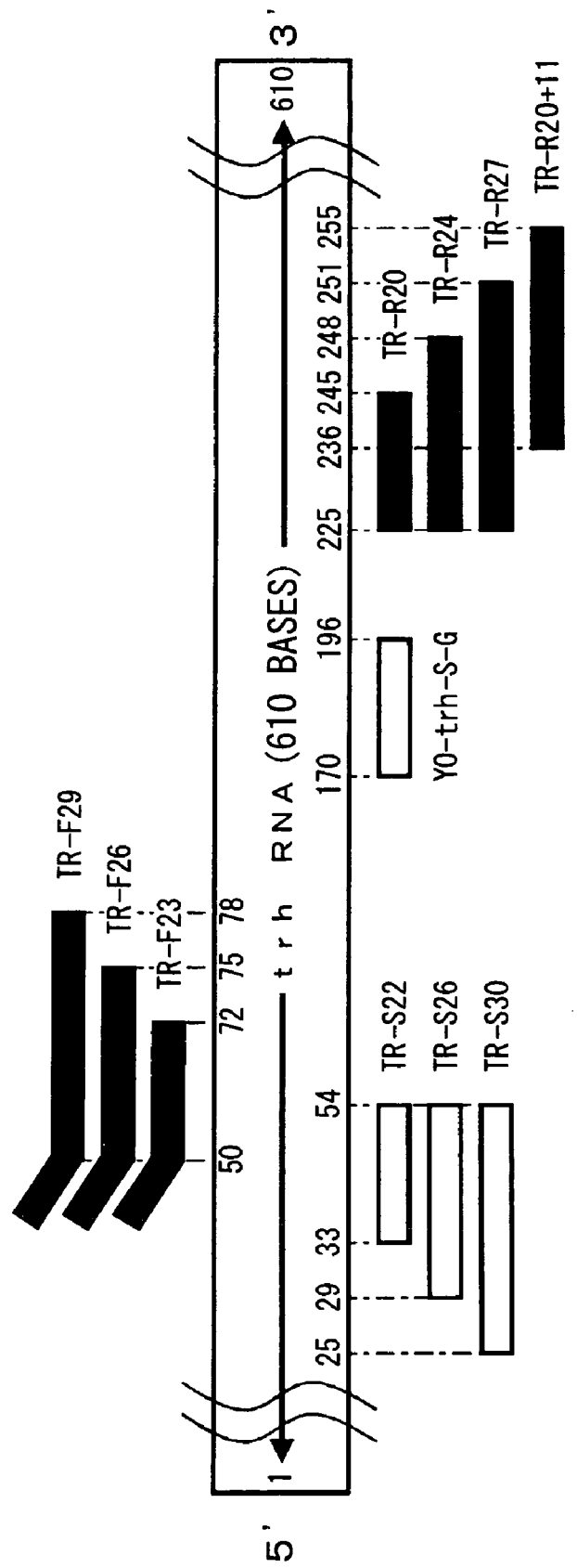
FIG. 1 shows the location of each oligonucleotide used in Example 1 along with the amplified regions. The base numbers in the drawing are in accordance with the literature (Appl. Environ. Microbiol., 58, 2449-2457 (1992)).

The following provides a detailed explanation of the present invention.

In the present invention, although the entire length of the base sequences listed in each of the sequence listings can be used for the first and second primers, respectively, as about 10 bases are sufficient for specific binding to a specific nucleic acid sequence or the like, a combination of at least 10 contiguous bases in each sequence may also be used.

The amplification process of the present invention includes the NASBA method, 3SR method or, for example, the RNA detection method (TRC method) described in Japanese Unexamined Patent Publication No. 2000-014400, which amplifies TRH1 and TRH2 RNA by concerted action of reverse transcriptase and RNA polymerase (by reacting them under a condition where the reverse transcriptase and RNA polymerase act in concert). Here, although there are no particular limitation on temperature, it is preferably 35 to 50° C.

In one aspect of the aforementioned invention of the present application, it is necessary for a target RNA to be cleaved at the 5' end of a specific sequence. A preferable method for cleaving the target RNA in this manner preferably consists of cleaving the target RNA with ribonuclease H, or the like, by adding an oligonucleotide having a sequence complementary to the region adjacent to and overlapping with the 5' end of the specific sequence (cleaving oligonucleotide). Said oligonucleotide is preferably an oligonucleotide consisting of a sequence listed as SEQ. ID No. 4, 5 or 6. In said cleaving oligonucleotide, the 3' end hydroxyl group is preferably chemically modified, for example, aminated, in order to suppress an elongation reaction from the 3' end.

Although the amplification product obtained in the aforementioned nucleic acid amplification method can be detected with a known nucleic acid detection method, in a preferable aspect of this method, the aforementioned nucleic acid amplification is preferably carried out in the presence of an oligonucleotide labeled with an intercalator fluorescent pigment followed by measurement of the change in the fluorescent properties of the reaction solution. In said oligonucleotide, as the intercalator fluorescent pigment is bound to the phosphorous atom in the oligonucleotide by means of a linker, the intercalator portion that forms a double strand with the target nucleic acid (complementary nucleic acid) intercalates to the double strand portion resulting in a change in fluorescent properties, thereby resulting in the characteristic of not requiring separation and analysis (Ishiguro, T. et al. (1996) Nucleic Acid Res. 24 (24) 4992-4997).

The sequence bound by the said oligonucleotide may be any sequence specific for TRH RNA and, although there are no particular limitations thereon, a sequence consisting of at least 10 contiguous bases in the sequence listed as SEQ. ID No. 3 or its complementary sequence is preferable. In addition, the hydroxyl group at the 3' end of said oligonucleotide is preferably chemically modified (such as by addition of glycolic acid) to suppress the elongation reaction which may occur by using this oligonucleotide as a primer.

As a result, TRH1 RNA and TRH2 RNA of *Vibrio parahaemolyticus* can be amplified and detected in a single tube, at a constant temperature and in a single step both rapidly and with high sensitivity, thereby facilitating application to automation.

Although the following provides a more detailed explanation of the invention of the present application through its examples, the present invention is not limited by these examples.

EXAMPLES

Example 1

The amplification efficiency of TRH RNA of *Vibrio parahaemolyticus* was compared for combinations (a) through (j) shown in Table 1 and FIG. 1.

(1) A sample of a standard RNA (616 bases) comprising base numbers 1 through 610 of TRH1 and TRH2 RNA of *Vibrio parahaemolyticus* (the base numbering of the RNA are in accordance with Nishibuchi, et al., Appl. Environ. Microbiol., 58, 2449-2457 (1992)) was quantified by ultraviolet absorption at 260 nm, and then diluted with an RNA diluent (10 mM Tris-HCl buffer (pH 8.0), 1 mM EDTA, 5 mM DTT, 0.5 U/µL RNase inhibitor (Takara Bio)) to $10^3$ copies/5 µL. Only diluent was used for the control group (negative control).

(2) 20 µL of a reaction solution having the composition indicated below was dispensed into 0.5 mL PCR tubes (Gene-Amp Thin-Walled Reaction Tubes, Applied Biosystems) followed by the addition of 5 µL of the aforementioned RNA sample thereto. Furthermore, solutions were prepared so that the combinations of the first primer, the second primer and the cleaving oligonucleotide were combined as shown in Table 1.

Composition of Reaction Solution (concentrations are shown as the concentration in the final reaction solution volume of 30 µL)
60 mM Tris-HCl buffer (pH 8.6)
17 mM magnesium chloride
130 mM potassium chloride (except that in combination (j), 100 mM)
6 U RNase inhibitor
1 mM DTT
0.25 mM each of dATP, dCTP, dGTP and dTTP
3.6 mM ITP
3.0 mM each of ATP, CTP, GTP and UTP
0.16 µM cleaving oligonucleotide
1.0 µM second primer
1.0 µM first primer
25 nM oligonucleotide labeled with intercalator pigment (YO-TRH—S-G, SEQ ID. No. 3; labeled with the intercalator fluorescent pigment between the 5th "C" and 6th "A" from the 5' end, and the hydroxyl group on its 3' end being modified with a glycol group.)
13% DMSO
Distilled Water for Adjusting Volume (3) After incubating the aforementioned reaction solution at 44° C. for 5 minutes, 5 µL of an enzyme solution having the composition indicated below and pre-heated for 2 minutes at 44° C. was added.

Composition of Enzyme Solution (values shown indicate the values for a final reaction solution volume of 30 µL)
2.0% sorbitol
3.6 µg bovine serum albumin
142 U T7 RNA polymerase (Invitrogen)
6.4 U AMV reverse transcriptase (Takara Bio)
Distilled Water for Adjusting Volume (4) Subsequently, the reaction solution in each of the PCR tubes was measured over time at an excitation wavelength of 470 nm and a fluorescent wavelength of 520 nm, while being incubated at 44° C., using a fluorescent spectrophotometer equipped with a temperature control function and capable of directly measuring the tube.

(5) The "rise time" result (the time required for the ratio in the fluorescence increase to reach 1.2 times the sum of the negative control sample's average value plus 3 standard deviations) obtained by using each oligonucleotide combination is shown in Table 2. As TRH1 and TRH2 RNA were detected within 15 minutes regardless of which combination (a) through (j) was used, the oligonucleotides used in these combinations were shown to be effective for detecting TRH RNA of *Vibrio parahaemolyticus*.

TABLE 1

| Combination | Cleaving Oligo. | Second primer | First primer | Amplification product length (bases) |
|---|---|---|---|---|
| (a) | TR-S22 | TR-F23 | TR-R21 | 202 |
| (b) | TR-S22 | TR-F23 | TR-R24 | 205 |
| (c) | TR-S22 | TR-F23 | TR-R27 | 208 |
| (d) | TR-S26 | TR-F26 | TR-R21 | 202 |
| (e) | TR-S26 | TR-F26 | TR-R24 | 205 |
| (f) | TR-S26 | TR-F26 | TR-R27 | 208 |
| (g) | TR-S30 | TR-F29 | TR-R21 | 202 |
| (h) | TR-S30 | TR-F29 | TR-R24 | 205 |
| (i) | TR-S30 | TR-F29 | TR-R27 | 208 |
| (j) | TR-S26 | TR-F26 | TR-R20 + 11 | 212 |

Table 1 shows the combinations of the first primer, the second primer and the cleaving oligonucleotide used in the experimental system along with the lengths of the specific bands amplified using those combinations. The locations and amplified regions of the oligonucleotides in TRH RNA of Vibrio parahaemolyticus are shown for each of the oligonucleotide combinations in FIG. 1. The hydroxyl group on the 3' end of the base sequence of the cleaving oligonucleotide was aminated. The region from the 1st "A" to the 22nd "A" from the 5' end of the base sequence of the second primer is a T7 promoter region, and the subsequent region of from the 23rd "G" to the 28th "A" is an enhancer sequence.

Cleaving Oligonucleotides:
  TR-S22 (SEQ. ID No. 4, base nos. 33 to 54)
  TR-S26 (SEQ. ID No. 5, base nos. 29 to 54)
  TR-S30 (SEQ. ID No. 6, base nos. 25 to 54)

Second Primers:
  TR-F23 (SEQ. ID No. 7, base nos. 50 to 72)
  TR-F26 (SEQ. ID No. 8, base nos. 50 to 75)
  TR-F29 (SEQ. ID No. 9, base nos. 50 to 78)

First Primers:
  TR-R21 (SEQ. ID No. 10, base nos. 225 to 245)
  TR-R24 (SEQ. ID No. 11, base nos. 225 to 248)
  TR-R27 (SEQ. ID No. 2, base nos. 225 to 251)
  TR-R20+11 (SEQ. ID No. 12, base nos. 236 to 255)

TABLE 2

| Combination | Rise time (min) | | | | | |
| --- | --- | --- | --- | --- | --- | --- |
| | trh1 $10^3$ copies/test | | | trh2 $10^3$ copies/test | | |
| (a) | 8.9 | 8.9 | 8.7 | 11.3 | 11.4 | 11.4 |
| (b) | 8.6 | 8.9 | 8.8 | 11.2 | 11.4 | 11.5 |
| (c) | 9.3 | 9.0 | 9.5 | 12.5 | 13.3 | 13.5 |
| (d) | 8.8 | 8.9 | 8.8 | 11.0 | 10.7 | 11.2 |
| (e) | 8.9 | 8.9 | 8.3 | 11.0 | 10.8 | 11.4 |
| (f) | 9.0 | 8.9 | 8.7 | 11.4 | 11.4 | 10.8 |
| (g) | 10.0 | 9.7 | 9.9 | 12.4 | 12.9 | 12.2 |
| (h) | 10.0 | 9.9 | 10.1 | 11.9 | 12.5 | 13.7 |
| (i) | 10.1 | 10.0 | 10.6 | 13.7 | 12.6 | 12.2 |
| (j) | 10.8 | 10.6 | 11.0 | 13.2 | 14.5 | 13.1 |

Table 2 shows the results of measuring TRH1 and TRH2 RNA at $10^3$ copies/test using the combinations of oligonucleotides shown in Table 1. All of the combinations of oligonucleotides shown in Table 1 detected TRH1 and TRH2 RNA within 15 minutes.

Example 2

Various initial numbers of copies of TRH1 and TRH2 RNA of Vibrio parahaemolyticus were detected using combination (j) shown in Table 1.

(1) TRH1 and TRH2 RNA of Vibrio parahaemolyticus similar to that of Example 1 were diluted to $10^7$ copies/5 μL to 10 copies/5 μL with an RNA diluent (10 mM Tris-HCl (pH 8.0), 1 mM EDTA, 5 mM DTT, 0.5 U/μL RNase inhibitor (Takara Bio)). Only diluent was used for the control group (negative control).

(2) 20 μL of a reaction solution having the composition indicated below was dispensed into PCR tubes (volume: 0.5 mL, GeneAmp Thin-Walled Reaction Tubes, Applied Biosystems) followed by the addition of 5 μL of the aforementioned RNA sample thereto.

Composition of Reaction Solution (concentrations are shown as the concentration in the final reaction solution volume of 30 μL)
  69 mM Tris-HCl buffer (pH 8.6)
  17.85 mM magnesium chloride
  100 mM potassium chloride
  6 U RNase inhibitor
  1 mM DTT
  0.25 mM each of dATP, dCTP, dGTP and dTTP
  3.6 mM ITP
  3.0 mM each of ATP, CTP, GTP and UTP
  0.16 μM cleaving oligonucleotide (TR-S26, SEQ. ID No. 5, hydroxyl group of its 3' end is aminated)
  1.0 μM second primer (TR-F26, SEQ. ID No. 8)
  1.0 μM first primer (TR-R20+11, SEQ. ID No. 12)
  25 nM oligonucleotide labeled with intercalator pigment (YO-TRH-S-G, SEQ ID. No. 3, labeled with the intercalator fluorescent pigment between the 5th "C" and 6th "A" from the 5' end, and the hydroxyl group on its 3' end being modified with a glycol group.)
  13% DMSO
  Distilled Water for Adjusting Volume (3) After incubating the aforementioned reaction solution at 44° C. for 5 minutes, 5 μL of an enzyme solution having the composition indicated below were added and pre-heated for 2 minutes at 44° C. were added.

Composition of Enzyme Solution (values shown indicate the values for a final reaction solution volume of 30 μL)
  2.0% sorbitol
  3.6 μg bovine serum albumin
  142 U T7 RNA polymerase (Invitrogen)
  6.4 U AMV reverse transcriptase (Takara Bio)
  Distilled Water for Adjusting Volume (4) Subsequently, the reaction solution in each of the PCR tubes was measured over time at an excitation wavelength of 470 nm and a fluorescent wavelength of 520 nm, while being incubated at 44° C., using a fluorescent spectrophotometer equipped with a temperature control function and capable of directly measuring the tube.

Setting the time of the addition of the enzyme as 0 min., the time-dependent changes in the fluorescent intensity ratio of the samples (fluorescent intensity value at predetermined time+background fluorescent intensity value) are shown in FIGS. 2(A) and 3(A). In addition, the results obtained for the relationship between the logarithmic value of the initial RNA amount and the "rise time" (the time required for the ratio in the fluorescence increase to reach 1.2 times the sum of the negative control sample's average value plus 3 standard deviations) are shown in FIGS. 2(B) and 3(B). Furthermore, the initial RNA amount ranged from 10 copies/test to $10^7$ copies/test.

Figure 2:
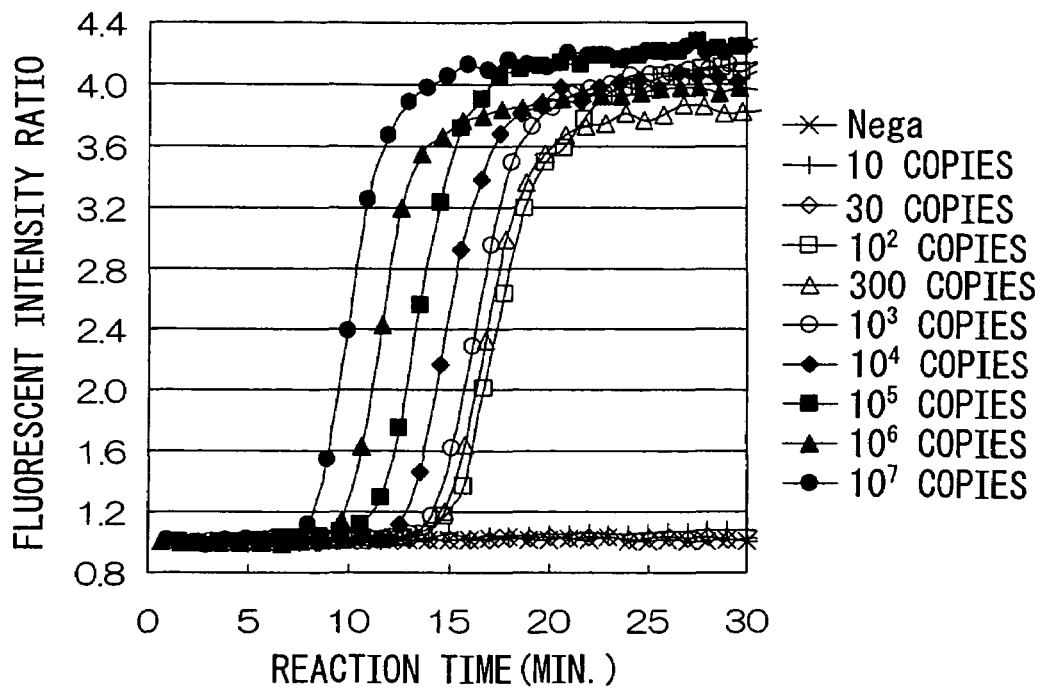
FIG. 2(A) shows a graph of the fluorescent intensity ratio that increases with the reaction time and the production of RNA from an initial amount of TRH1 RNA of 10 copies/test to $10^7$ copies/test carried out in Example 2, and (B) shows a calibration curve obtained between the logarithmic value of the initial RNA amount and the rise time. "Nega" refers to a sample in which diluent was used instead of an RNA sample. TRH1 RNA for which the initial RNA amount was $10^2$ copies/test was capable of being detected at a reaction time of about 15 minutes, and a correlation was observed between the initial RNA amount and the rise time.
Figure 2:
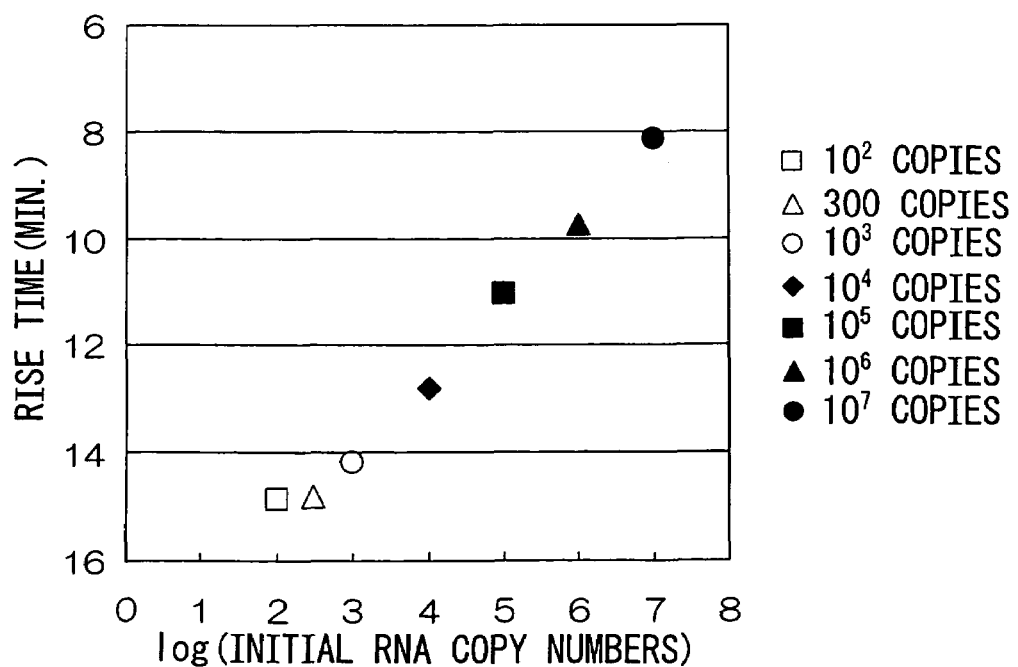
Figure 3:
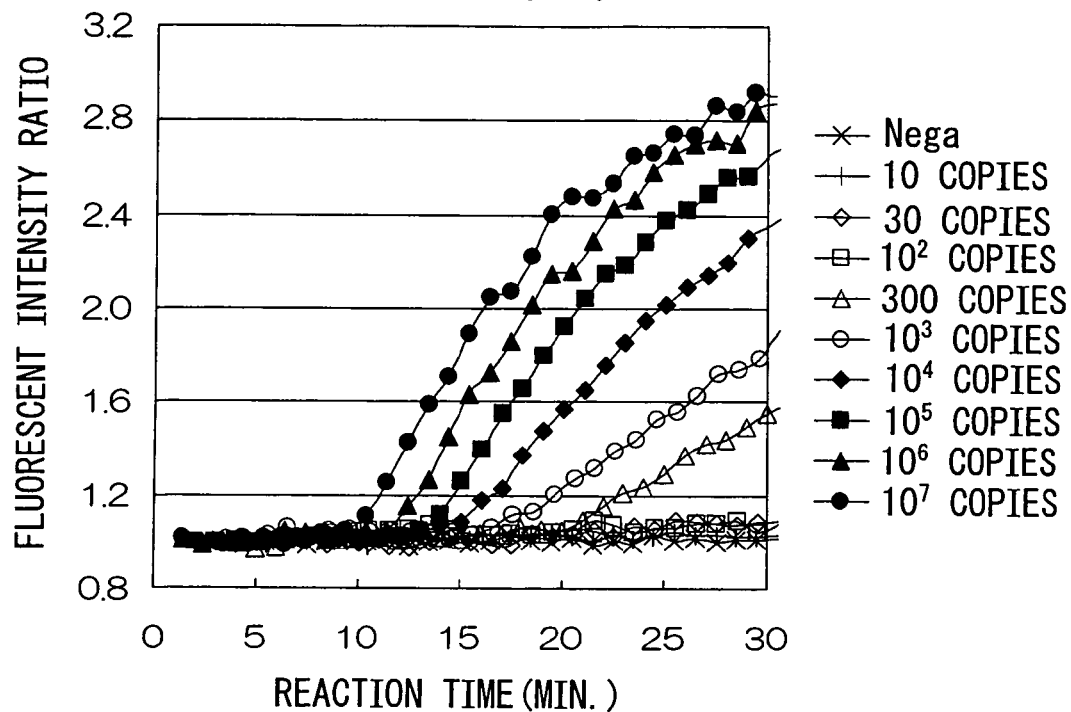
FIG. 3(A) shows a graph of the fluorescent intensity ratio that increases with the reaction time and the production of RNA from an initial amount of TRH2 RNA of 10 copies/test to 1 copies/test carried out in Example 2, and (B) shows a calibration curve obtained between the logarithmic value of the initial RNA amount and the rise time. "Nega" refers to a sample in which diluent was used instead of an RNA sample. TRH2 RNA for which the initial RNA amount was $10^3$ copies/test could be detected after a reaction time of about 19 minutes, and a correlation was observed between the initial RNA amount and the rise time.
Figure 3:
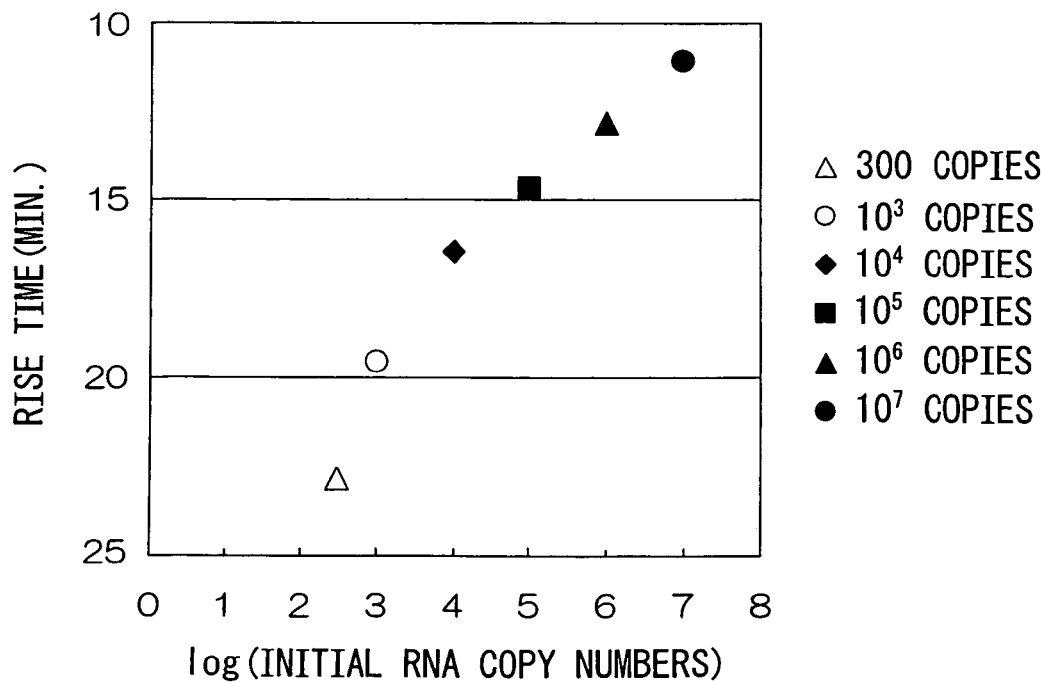

According to FIGS. 2 and 3, $10^2$ copies were detected in about 15 minutes in the case of TRH1 RNA, while $10^3$ copies were detected in about 19 minutes in the case of TRH2 RNA. In addition, as the present combination detected TRH1 and TRH2 RNA even in an initial amount of $10^3$ copies/test within 20 minutes, it is possible to carry out simultaneous detection of TRH1 and TRH2 RNA more rapidly and with higher sensitivity as compared with the methods of the prior art (Japanese Unexamined Patent Publications Nos. 2001-340087 and 2001-340088).

INDUSTRIAL APPLICABILITY

As has been explained above, the detection method of the invention of the present application is useful for detecting TRH1 and TRH2 RNA of *Vibrio parahaemolyticus* both simultaneously and with high sensitivity.

The oligonucleotide of the invention of the present application is not limited to that of the base sequences listed in the sequence listings (having 22 to 30 bases), but rather can be a nucleotide comprised of at least 10 contiguous bases in those sequences. This is because it is clear that a base sequence of about 10 bases is sufficient for ensuring specificity to a target nucleic acid of a primer or probe under comparative low-temperature (preferably 44° C.) conditions.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

The invention claimed is:

1. A composition comprising:
   an isolated first primer which consists of SEQ ID NO:12;
   an isolated second primer which consists of SEQ ID NO:8.

2. The composition according to claim 1, further comprising a cleaving oligonucleotide consisting of SEQ ID NO: 4, 5 or 6.

3. The composition according to claim 1, further comprising an oligonucleotide labeled with an intercalator fluorescent pigment.

4. The composition according to claim 3, wherein the oligonucleotide labeled with the intercalator fluorescent pigment consists of at least 10 contiguous bases of the sequence listed as SEQ ID NO: 3.

5. The composition of claim 1, further comprising a cleaving oligonucleotide, which may be chemically modified.

6. The composition of claim 1, further comprising at least one TRH1 or TRH2 RNA, or both.

7. The composition of claim 1, further comprising the reagents necessary for performing an RNA amplification.

8. The composition of claim 1, further comprising at least one member of the group consisting of an RNA template derived from a TRH 1 gene, an RNA template derived from a TRH 2 gene, an RNA-dependent polymerase, ribonuclease H and a DNA-dependent DNA polymerase.

* * * * *

```
                              SEQUENCE LISTING

<160> NUMBER OF SEQ ID NOS: 12

<210> SEQ ID NO 1
<211> LENGTH: 29
<212> TYPE: DNA
<213> ORGANISM: Artificial Sequence
<220> FEATURE:
<223> OTHER INFORMATION: Synthetic DNA

<400> SEQUENCE: 1
actctacttt gctttcagtt tgctattgg                                         29

<210> SEQ ID NO 2
<211> LENGTH: 27
<212> TYPE: DNA
<213> ORGANISM: Artificial Sequence
<220> FEATURE:
<223> OTHER INFORMATION: Synthetic DNA

<400> SEQUENCE: 2
ttttcttttt atgtttcggt ttgtcca                                           27

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
gattcagttt ttattgttgt atttcta                                           27

<210> SEQ ID NO 4
<211> LENGTH: 22
<212> TYPE: DNA
<213> ORGANISM: Artificial Sequence
<220> FEATURE:
<223> OTHER INFORMATION: Synthetic DNA

<400> SEQUENCE: 4
agagttttag tttcataatt aa                                                22

<210> SEQ ID NO 5
<211> LENGTH: 26
<212> TYPE: DNA
<213> ORGANISM: Artificial Sequence
<220> FEATURE:
<223> OTHER INFORMATION: Synthetic DNA

<400> SEQUENCE: 5
agagttttag tttcataatt aatcct                                            26
```

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
agagttttag tttcataatt aatcctttat                               30

<210> SEQ ID NO 7
<211> LENGTH: 51
<212> TYPE: DNA
<213> ORGANISM: Artificial Sequence
<220> FEATURE:
<223> OTHER INFORMATION: Synthetic DNA

<400> SEQUENCE: 7
aattctaata cgactcacta tagggagaac tctactttgc tttcagtttg c       51

<210> SEQ ID NO 8
<211> LENGTH: 54
<212> TYPE: DNA
<213> ORGANISM: Artificial Sequence
<220> FEATURE:
<223> OTHER INFORMATION: Synthetic DNA

<400> SEQUENCE: 8
aattctaata cgactcacta tagggagaac tctactttgc tttcagtttg ctat    54

<210> SEQ ID NO 9
<211> LENGTH: 57
<212> TYPE: DNA
<213> ORGANISM: Artificial Sequence
<220> FEATURE:
<223> OTHER INFORMATION: Synthetic DNA

<400> SEQUENCE: 9
aattctaata cgactcacta tagggagaac tctactttgc tttcagtttg ctattgg    57

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
ttttatgttt cggtttgtcc a                                        21

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA

<400> SEQUENCE: 11
tctttttatg tttcggtttg tcca                                     24

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA -continued

```
<400> SEQUENCE: 12
atggttttct ttttatgttt                                                    20
```